US006995180B2

(12) United States Patent
Magnin et al.

(10) Patent No.: US 6,995,180 B2
(45) Date of Patent: Feb. 7, 2006

(54) GLYCINENITRILE-BASED INHIBITORS OF DIPEPTIDYL PEPTIDASE IV AND METHODS

(75) Inventors: David R. Magnin, Hamilton, NJ (US); Lawrence G. Hamann, Cherry Hill, NJ (US)

(73) Assignee: Bristol Myers Squibb Company, Princeton, NJ (US)

(*) Notice: Subject to any disclaimer, the term of this patent is extended or adjusted under 35 U.S.C. 154(b) by 250 days.

(21) Appl. No.: 10/690,173

(22) Filed: Oct. 21, 2003

(65) Prior Publication Data

US 2004/0259919 A1 Dec. 23, 2004

Related U.S. Application Data

(60) Provisional application No. 60/420,603, filed on Oct. 23, 2002.

(51) Int. Cl.
A61K 31/44 (2006.01)
A61K 31/275 (2006.01)
C07D 211/30 (2006.01)
C07C 255/03 (2006.01)

(52) U.S. Cl. ............... 514/357; 514/527; 546/247; 558/390

(58) Field of Classification Search ............ 546/247; 558/390; 514/357, 527
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau, II et al. |
| 5,612,359 A | 3/1997 | Murugesan |
| 5,614,492 A | 3/1997 | Habener |
| 5,631,224 A | 5/1997 | Efendic et al. |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky |
| 6,043,265 A | 3/2000 | Murugesan et al. |

FOREIGN PATENT DOCUMENTS

| | | |
|---|---|---|
| EP | 0 142 146 | 5/1985 |
| EP | 0 221 025 | 5/1987 |
| FR | 2 596 393 | 10/1987 |
| GB | 2 205 837 | 12/1988 |
| WO | WO 86/03488 | 6/1986 |
| WO | WO 86/07054 | 12/1986 |

(Continued)

OTHER PUBLICATIONS

Ashworth, D.M. et al., "2-Cyanopyrrolidides as Potent, Stable Inhibitors of Dipeptidyl Peptidase IV", Bioorganic & Medicinial Chemistry Letters, vol. 6, No. 10, pp. 1163-1166 (1996).

(Continued)

Primary Examiner—Johann Richter
Assistant Examiner—Ebenezer Sackey
(74) Attorney, Agent, or Firm—Jonathan N. Provoost; Maureen P. O'Brien

(57) ABSTRACT

A compound of the formula I:

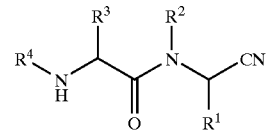

wherein $R^1$, $R^2$, $R^3$ and $R^4$ are as defined herein.

Further provided are methods of using such compounds for the treatment of diabetes and related diseases, and to pharmaceutical compositions containing such compounds.

18 Claims, No Drawings

FOREIGN PATENT DOCUMENTS

| WO | WO 96/38144 | 12/1996 |
|---|---|---|
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO2004/037181 | 5/2004 |

OTHER PUBLICATIONS

Ashworth, D.M. et al., "4-Cyanothiazolidides as Very Potent, Stable Inhibitors of Dipeptidyl Peptidase IV", Bioorganic & Medicinial Chemistry Letters, vol. 6, No. 22, pp. 2745-2748 (1996).

Biller, S.A. et al., "Isoprenoid (Phosphinylmethyl) phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, pp. 1-40 (1996).

Bundgaard, H., Chapter 5: "Design and Application of Prodrugs", A Textbook of Drug Design and Development, Harwood Academic Publishers, publ., Krogsgaard-Larsen, P. and Bundgaard, T., eds., pp. 113-191 (1991).

Bundgaard, H., ed., Design of Prodrugs, Elsevier Science Publishers B.V., publ. (1985) (table of contents).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, pp. 11-20 (1999).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Hanessian, S. et al., "Probing the Importance of Spacial and Conformational Domains in Captopril Analogs for Angiotensin Converting Enzyme Activity", Bioorganic & Medicinal Chemistry Letters, vol. 8, pp. 2123-2128 (1998).

Hara, S., "Ileal $Na^+$/bile acid cotransporter inhibitors", Drugs of the Future, vol. 24, No. 4, pp. 425-430 (1999).

Hughes, T.E. et al., "(1-[[[2-[(5-Cyanopyridin-2-yl)amino] ethyl]amino]acetyl]-2-cyano-(S)-pyrrolidine), a Slow-Binding Inhibitor of Dipeptidyl Peptidase IV", Biochemistry, vol. 38, pp. 11597-11603 (1999).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinial Endocrinology and Metabolism, vol. 82, No. 3, pp. 727-734 (1997).

Krause, B.R. et al., Chapter 6: "ACAT Inhibitors: Physiologic Mechanisms for Hypolipidemic and Anti-Atherosclerotic Activities in Experimental Animals", Inflammation: Mediators Pathways, CRC Press, Inc., publ., Ruffolo, Jr., R.R. and Hollinger, M.A., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C-Analogues of Isopentenyl Diphosphate and Dimethylallyl Diphospate and Dimethylally Diphosphate", J. Am. Chem. Soc:, vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ—Effect of PPAR-α Activation on Abnormal Lipid Metabolism in Liver of Zucker Fatty Rats", Diabetes, vol. 47, pp. 1841-1847 (1998).

Nagatsu, T. et al., "New Chromogenic Substrates for X-Prolyl Dipeptidyl-Aminopeptidase", Analytical Biochemistry, vol. 74, pp. 466-476 (1976).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Oritz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rahfeld, J. et al., "Extended Investigation of the Substrate Specificity of Dipeptidyl Peptidase IV from Pig Kidney", Biol. Chem. Hoppe-Seyler, vol. 372, pp. 313-318 (1991).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Sagnard, I. et al., "Enantioselective Synthesis of Cyclopropane α-Amino Acids: Synthesis of N-Boc-cis-(2S, 3R,4S)-3,4-Methanoproline and N-Boc-(2S,3R,4S)-3,4,-Methanoglutamic Acid", Tetrahedron Letters, vol. 36, No. 18, pp. 3149-3152 (1995).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, pp. 204-225 (1994).

Smith, C. et al., "RP 73163: A bioavailable Alkysulphinyl-Diphenylimidazole ACAT Inhibitor, Bioorganic & Medicinal Chemistry Letters", vol. 6, No. 1, pp. 47-50 (1996).

Sorbera, L.A. et al., "Avasimibe: Treatment of Lipoprotein Disorders—ACAT Inhibitor", Drugs of Future, vol. 24, No. 1, pp. 9-15 (1999).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Tverezovsky, V.V. et al., "Synthesis of (2S, 3R, 4S)-3,4-Methanoproline and Analogues by Cyclopropylidene Insertion", Tetrahedron, vol. 53, No. 43, pp. 14773-14792 (1997).

Wermuth, C.G. et al., Chapter 31: "Designing Prodrugs and Bioprecursors I: Carrier Prodrugs", The Practice of Medicinal Chemistry, Academica Press, publ., Wermuth, C.G., ed., pp. 671-696 (1996).

Yamada, M. et al., "A Potent Dipeptide Inhibitor of Dipeptidyl Peptidase IV", Bioorganic & Medicinal Chemistry Letters, vol. 8, pp. 1537-1540 (1998).

GLYCINENITRILE-BASED INHIBITORS OF DIPEPTIDYL PEPTIDASE IV AND METHODS

CROSS-REFERENCE TO RELATED APPLICATION

This application claims the benefit of U.S. Provisional Application No. 60/420,603 filed Oct. 23, 2002, incorporated herein by reference in its entirety

FIELD OF THE INVENTION

The present invention relates to glycinenitrile-based inhibitors of dipeptidyl peptidase IV (DPP-4), and to a method for treating diabetes, especially Type II diabetes, as well as hyperglycemia, hypoglycemia, Syndrome X, diabetic complications, hyperinsulinemia, obesity, atherosclerosis and related diseases, anxiety, eating disorders, neurodegenerative diseases, as well as various immunomodulatory diseases including psoriasis, multiple sclerosis, rheumatoid arthritis, and chronic inflammatory bowel disease, and for organ transplantation employing such glycinenitrile compounds alone or in combination with another therapeutic agent.

BACKGROUND OF THE INVENTION

Dipeptidyl peptidase IV (DPP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, GIP, NPY, GLP-2, VIP) in vitro.

GLP-1(7-36) is a 29 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo ($t_{1/2} \approx 1.5$ min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1(7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36) and thus serve to ameliorate the diabetic condition.

SUMMARY OF THE INVENTION

In accordance with the present invention, glycinenitrile-based compounds are provided having the structure of formula I:

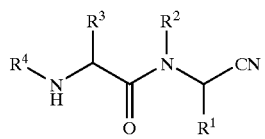

I wherein:
$R^1$ is selected from the group consisting of hydrogen (H), $C_1$–$C_6$ alkyl, $C_3$–$C_8$ cycloalkyl and $C_3$–$C_8$ cycloalkenyl;

$R^2$ is a substituted or unsubstituted functional group selected from the group consisting of $C_1$–$C_6$ alkyl, $C_3$–$C_8$ cycloalkyl, $C_3$–$C_8$ cycloalkenyl, alkenyl, alkynyl, aryl, arylalkyl, arylalkenyl and arylalkynyl;

$R^3$ is selected from the group consisting of alkyl, alkenyl, alkynyl, cycloalkyl, cycloalkylalkyl, alkylthioalkyl, arylalkylthioalkyl, cycloalkenyl, aryl, arylalkyl, arylalkenyl, arylalkynyl heteroaryl, heteroarylalkyl, cycloheteroalkyl and cycloheteroalkylalkyl, wherein any $R^3$ group, as defined herein may optionally be substituted through any available carbon atom with 1 to 5 substituents selected from the group consisting of hydrogen, halo, alkyl, polyhaloalkyl, alkoxy, haloalkoxy, alkoxycarbonyl, alkenyl, alkynyl, cycloalkyl, cycloalkylalkyl, heteroarylamino, —N($R^5$)Ar, cycloheteroalkyl, cycloheteroalkylalkyl, $OR^5$, hydroxyalkyl, nitro, cyano, $NR^5R^{5'}$, alkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

$R^4$ is hydrogen(H), or $R^4$ can be taken together with $R^3$ to form a substituted or unsubstituted 4 to 5 membered heterocyclic ring, preferably substituted by $NR^5R^{5'}$ or $C_1$–$C_6$ alkyl; and $R^5$ and $R^{5'}$ for each occurrence are each independently selected from the group consisting of hydrogen, alkyl, alkenyl, alkynyl, cycloalkyl, aryl, arylalkyl, arylalkenyl, arylalkynyl, heterocycle and heteroaryl.

The definition of formula I above includes all pharmaceutically acceptable salts, stereoisomers, and prodrug esters of formula I.

The compounds of formula I possess activity as inhibitors of DPP-4 in vivo and are useful in the treatment of diabetes and the micro- and macrovascular complications of diabetes such as retinopathy, neuropathy, nephropathy, and wound healing.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

Preferred are compounds of formula I wherein
$R^1$ is H or $C_1$–$C_6$ alkyl;
$R^2$ is $C_1$–$C_6$ alkyl;
$R^3$ is alkyl or cycloalkyl; and
$R^4$ is H.

Further embodiments of the invention include compounds of formula I wherein $R^1$ is H; $R^2$ is $C_1$–$C_6$ alkyl; $R^3$ is cycloalkyl or polycycloalkyl from 6 to 15 carbons; and $R^4$ is H.

DETAILED DESCRIPTION OF THE INVENTION

The following abbreviations are employed in the Examples and elsewhere herein:
i-Bu=iso-butyl
FMOC=fluorenylmethoxycarbonyl
Boc or BOC=tert-butoxycarbonyl
Cbz=carbobenzyloxy or carbobenzoxy or benzyloxycarbonyl
HOAc or AcOH=acetic acid
DMF=N,N-dimethylformamide
DMSO=dimethyl sulfoxide
PTFE=polytetrafluoroethylene
EtOAc=ethyl acetate
THF=tetrahydrofuran
TFA=trifluoroacetic acid
$Et_2NH$=diethylamine
NMM=N-methyl morpholine
Pd/C=palladium on carbon
TEA=triethylamine
EDAC=3-ethyl-3'-(dimethylamino)propyl-carbodiimide hydrochloride (or 1-[(3-(dimethyl)amino)propyl])-3-ethylcarbodiimide hydrochloride)
HOBT or HOBT·$H_2O$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
min=minute(s)
L=liter
mL=milliliter
μL=microliter
g=gram(s)
mg=milligram(s)
mol=mole(s)
mmol=millimole(s)
rt=room temperature
aq=aqueous MS or Mass Spec=mass spectrometry
NMR=nuclear magnetic resonance The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 20 carbons, preferably 1 to 10 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such alkyl groups including 1 or more substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

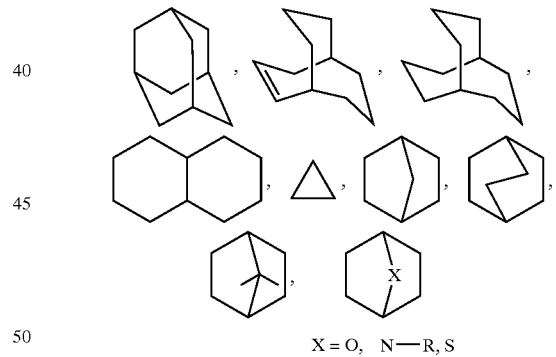

X = O, N—R, S any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally an alkenyl group may be substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and said alkynyl groups may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl or cycloheteroalkyl rings for example

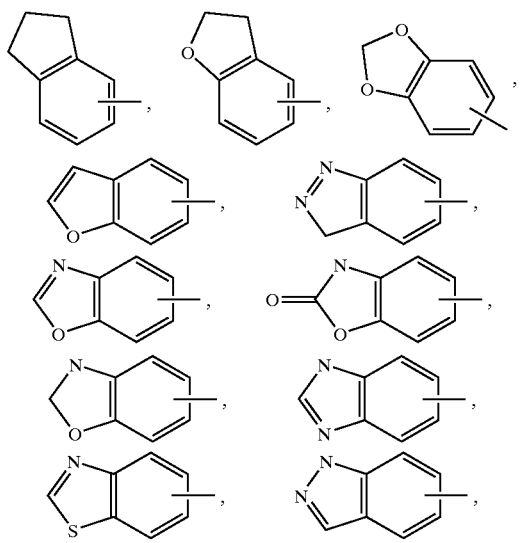

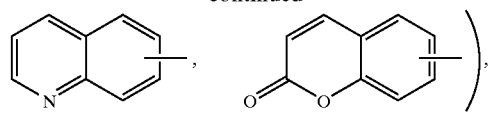

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl and/or any of the alkyl substituents set out herein.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

Unless otherwise indicated, the term "alkoxy", "aryloxy" or "arylalkoxy" as employed herein alone or as part of another group includes any of the above alkyl, arylalkyl or aryl groups linked to an oxygen atom.

Unless otherwise indicated, the term alkylthio", "arylthio" or "arylalkylthio" as employed herein alone or as part of another group includes any of the above alkyl, arylalkyl or aryl groups linked through a sulfur atom.

Unless otherwise indicated, the term "alkylamino", "arylamino", or "arylalkylamino" as employed herein alone or as part of another group includes any of the above alkyl, aryl or arylalkyl groups linked through a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as:

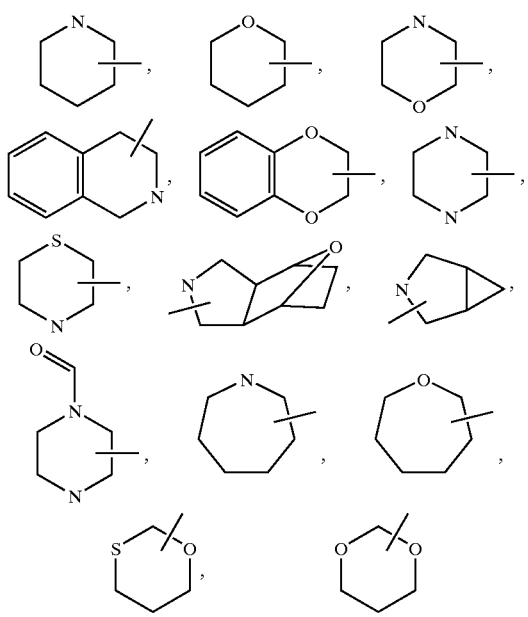

and the like. The above groups may include 1 to 4 substituents such as alkyl, halo, hydroxy, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

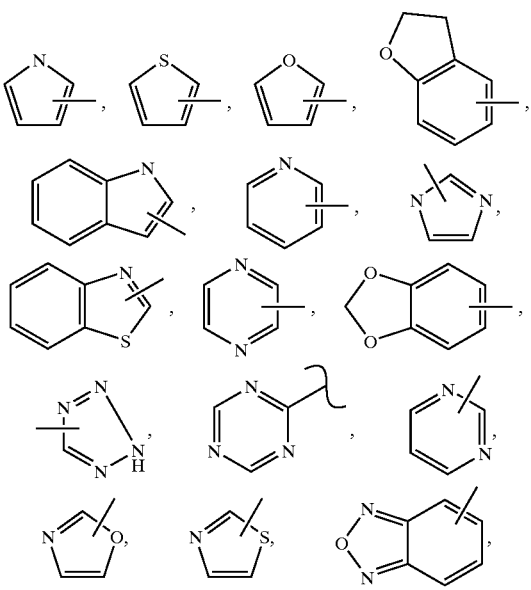

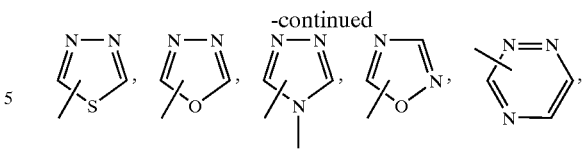

and the like.

The term "cycloheteroalkylalkyl" as used herein alone or as part of another group refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a $-(CH_2)_r-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "haloalkoxy" as used herein refers to an "alkoxy" group as defined above which includes from 1 to 9, preferably from 2 to 5, halo substituents, such as F or Cl, preferably F, such as $CF_3CH_2O-$, $CF_3O-$ or $CF_3CF_2CH_2O-$.

The term "cycloalkylalkyl" as used herein refers to a cycloalkyl alkyl group linked throgh an alkyl group.

The term "halogen" or "halo" as used herein alone or as part of another group refers to chlorine, bromine, fluorine, and iodine.

The term "polyhaloalkyl" as used herein refers to an "alkyl" group as defined above which includes one or more halo substituents, such as F or Cl, preferably F, such as $CF_3CH_2-$, $CF_3-$ or $CF_3CF_2CH_2-$.

The term "heterocyclo", "heterocycle" or "heterocyclic ring", as used herein, represents an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The term "thiol" or "thio" as used herein, refers to (—S) or (—S—).

The term "alkylthio" refers to an alkyl group linked to the parent molecular moiety through a thiol group.

The term "alkylthioalkyl" refers to an alkylthio group linked to the parent molecular moiety through an alkyl group.

The term "arylalkylthioalkyl" refers to Ar-alkyl-S-alkyl-.

The term "alkoxycarbonyl," as used herein, refers to an alkoxy group, as defined herein, appended to the parent molecular moiety through a carbonyl group, as defined herein.

The term "cyano," as used herein, refers to a —CN group.

The term "carboxyl" denotes —C(O)O—.

The term "nitro" as used herein, refers to a —NO$_2$ group.

The term "sulfonyl" as used herein, refers to an SO$_2$ group

The term "sulfinyl" as used herein, refers to an SO group

The term "hydroxyalkyl" as used herein, refers to an "alkyl" or "cycloalkyl" group as defined above which preferably includes from 1 to 3 hydroxy substituents The term "aminocarbonyl" refer to an amino group, herein a NR$^5$R$^{5\prime}$ group, linked through a carbonyl group, as defined herein, to the parent molecular moiety.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a.) *The Practice of Medicinal Chemistry*, Camille G. Wermuth et al., Ch 31, (Academic Press, 1996);

b.) *Design of Prodrugs*, edited by H. Bundgaard, (Elsevier, 1985); and c.) *A Textbook of Drug Design and Development*, P. Krogsgaard-Larson and H. Bundgaard, eds. Ch 5, pgs 113–191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I include hydrochloride or trifluoroacetic acid salts The compounds of formula I of the invention can be prepared as shown in the following reaction schemes and description thereof, as well as relevant published literature procedures that may be used by one skilled in the art. Exemplary reagents and procedures for these reactions appear hereinafter in the working Examples.

Scheme 1

Step 1.

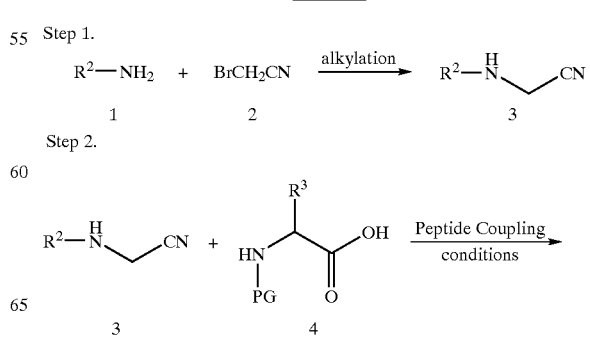

Step 2.

-continued

Step 3.

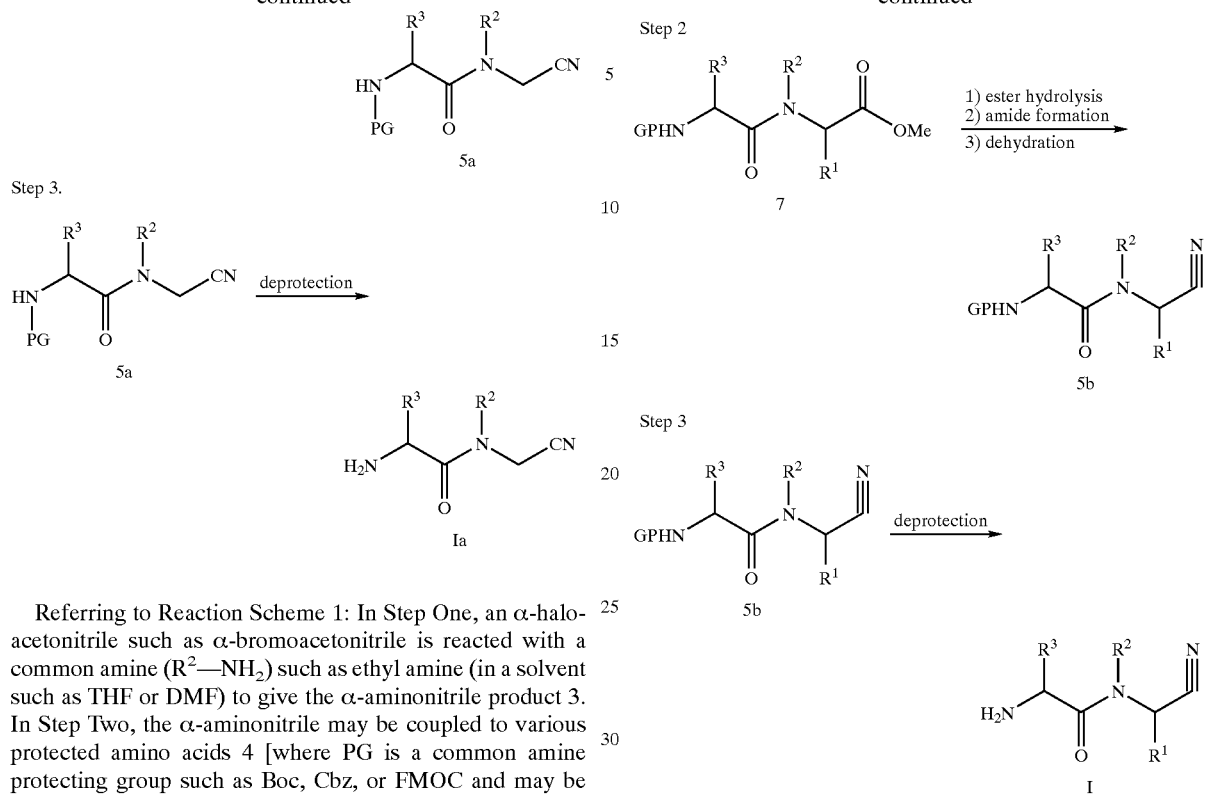

Referring to Reaction Scheme 1: In Step One, an α-haloacetonitrile such as α-bromoacetonitrile is reacted with a common amine ($R^2$—$NH_2$) such as ethyl amine (in a solvent such as THF or DMF) to give the α-aminonitrile product 3. In Step Two, the α-aminonitrile may be coupled to various protected amino acids 4 [where PG is a common amine protecting group such as Boc, Cbz, or FMOC and may be generated by methods as described herein or in the literature (for example, see Sagnard et al, Tet-Lett., 1995, 36, pp. 3148–3152, Tverezovsky et al, Tetrahedron, 1997, 53, pp. 14773–14792, Hanessian et al, Bioorg. Med. Chem. Lett., 1998, 8, p. 2123–2128)] using standard peptide coupling conditions (e.g. EDAC/HOAT, i-BuCOCOCl/TEA, PyBop/NMM) to afford the corresponding dipeptide nitrile 5. In Step Three, the dipeptide nitrile is deprotected to give the final products. Removal of the PG group by conventional methods (e.g. (1) TFA [isolates the trifluoroacetic acid salt] or HCl [isolates the hydrocholoride salt] when PG is Boc, or (2) $H_2$/Pd/C, TMSI when PG is Cbz, or (3) $Et_2$NH when PG is (FMOC)) affords the compound of formula Ia where $R^1$ is hydrogen.

Scheme 2

Step 1

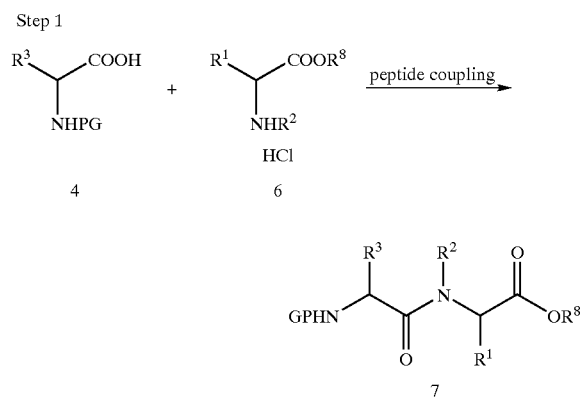

In a different reaction sequence (Scheme 2), a dipeptide ester (7) is formed under any one of a variety of standard peptide coupling conditions as described above (where $R^8$ is alkyl or arylalkyl group such as methyl, ethyl, t-butyl, benzyl, or substituted benzyl). The dipeptide ester may then be hydrolyzed to the acid under a variety of conditions such as sodium or potassium hydroxide in a suitable solvent such as methanol, THF, or dioxane to provide the acid. Conversion of the acid to the amide may be effected by activation of the acid group (e.g. employing i-BuOCOCl/TEA, EDAC, or MsCl/Hunigs base) followed by treatment with $NH_3$ or an ammonia equivalent in a solvent such as dioxane, ether, methanol, $CH_2Cl_2$. The amide group may be converted to a nitrile 5b under a variety of standard conditions (e.g. $POCl_3$/imidazole/pyridine, or cyanuric chloride/DMF). Removal of the PG group as described above affords compounds of formula I where $R^4$ is hydrogen.

Scheme 2a

Step 1

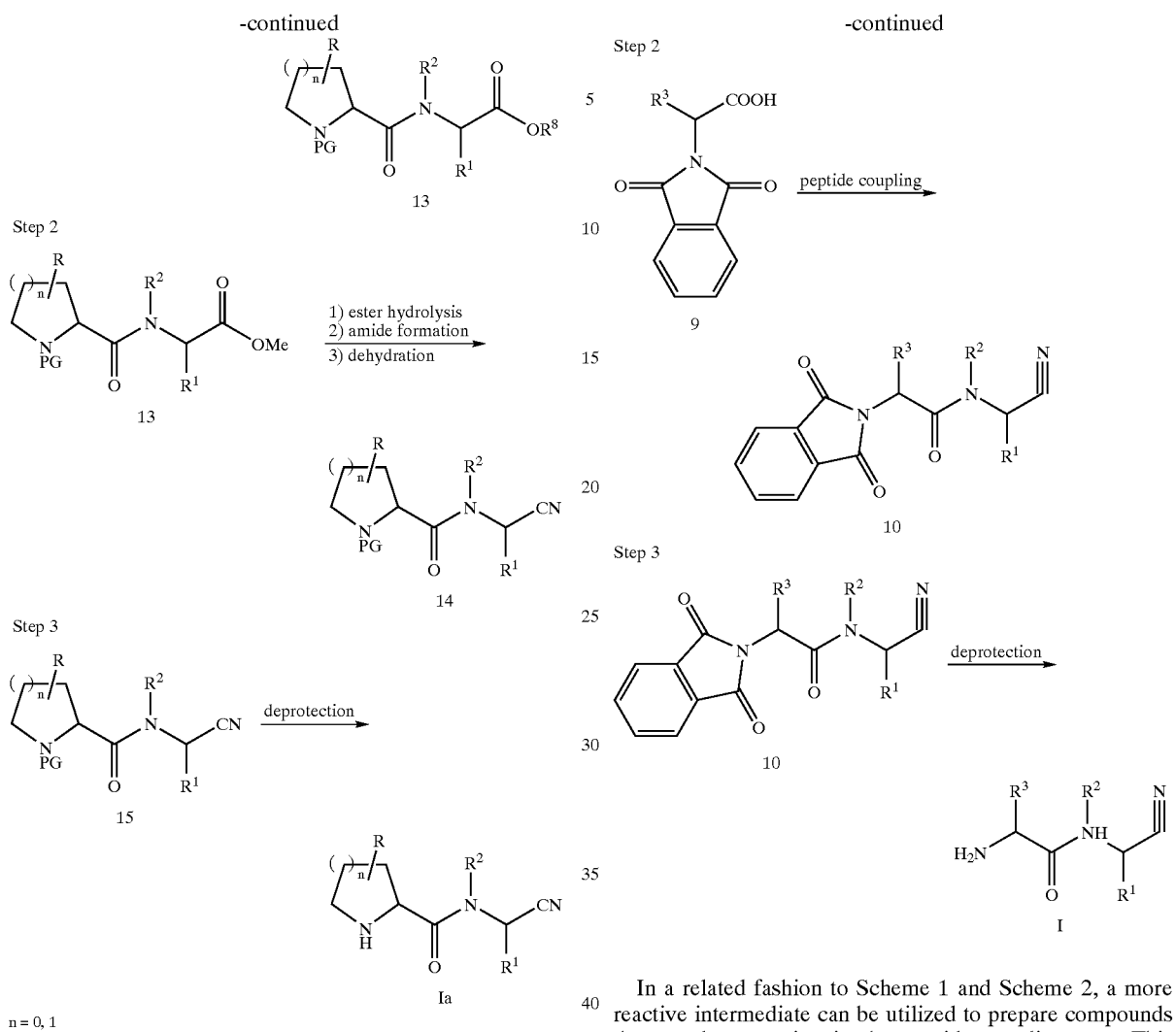

Using the same chemistry as described for Scheme 2, compounds of formula I where R4 is taken together with R3 to form a substituted or unsubstituted 4 to 5 membered heterocyclic ring. Additional heteroatoms may be included in the heterocyclic ring as provided by the definition of "heterocyclic" herein. "R" represents H or one or more substitutients attached at any available carbon or heteroatom, as defined herein.

Scheme 3

Step 1

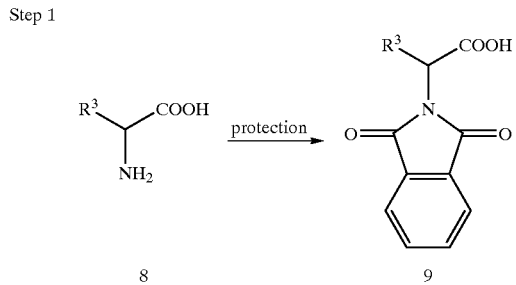

In a related fashion to Scheme 1 and Scheme 2, a more reactive intermediate can be utilized to prepare compounds that are less reactive in the peptide coupling step. This sequence uses the phthalimide protection of the amino group and invokes either preparation of the acid chloride (or a mixed anhydride of comparable reactivty, e.g. mesylate) for the peptide coupling sequence. In Step One an amino acid is protected as the phthalamide (phthalic anhydride, heat). In Step Two the acid is converted to the acid chloride using $(COCl)_2$ with DMF as a catalyst. The acid chloride is then coupled with an α-amino nitriles to give a dipeptidenitrile 10. In Step Three deprotection with $N_2H_4$ in a solvent, such as methanol, to provide compounds of formula I where $R^4$ is hydrogen.

Utility & Combinations

A. Utilities

The compounds of the present invention possess activity as inhibitors of the dipeptidyl peptidase IV which is found in a variety os tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

Accordingly, the compounds of the present invention can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may employed in combination with other inhibitors of DPP-4 activity or other suitable therapeutic agents useful in the treatment of the aforementioned disorders including: anti-diabetic agents; anti-hyperglycemic agents; hypolipidemic/lipid lowering agents; anti-obesity agents; anti-hypertensive agents and appetite supressants.

Examples of suitable anti-diabetic agents for use in combination with the compounds of the present invention include biguanides (e.g., metformin or phenformin), glucosidase inhibitors (e.g,. acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®, thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1), and SGLT2 inhibitors.

It is believed that the use of the compounds of formula I in combination with at least one or more other antidiabetic agent(s) provides antihyperglycemic results greater than that possible from each of these medicaments alone and greater than the combined additive anti-hyperglycemic effects produced by these medicaments.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. application Ser. No. 09/644,598, filed Sep. 18, 2000, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Other suitable DPP4 inhibitors that may be used in combination with the compounds of the invention include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides, as disclosed by Ashworth et al, Bioorg. & Med. Chem. Lett., Vol. 6, No. 22, pp 1163–1166 and 2745–2748 (1996) employing dosages as set out in the above references.

Suitable meglitinides include nateglinide (Novartis) or KAD1229 (PF/Kissei).

Examples of suitable anti-hyperglycemic agents for use in combination with the compounds of the present invention include glucagon-like peptide-1 (GLP-1,) such as GLP-1(1-36) amide, GLP-1(7-36) amide, GLP-1(7-37) (as disclosed in U.S. Pat. No. 5,614,492 to Habener), as well as AC2993 (Amylen) and LY-315902 (Lilly).

Examples of suitable hypolipidemic/lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative)

dichloroacetate, imidazole analogs of mevalonolactone, as disclosed in PCT application WO 86/07054, 3-carboxy-2-hydroxy-propane-phosphonic acid derivatives, as disclosed in French Pat. No. 2,596,393, 2,3-disubstituted pyrrole, furan and thiophene derivatives, as disclosed in European Pat. Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Pat. Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

The fibric acid derivatives which may be employed in combination with one or more compounds of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA: cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425–430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a beta 3 adrenergic agonist, a lipase inhibitor, a serotonin (and dopamine) reuptake inhibitor, a thyroid receptor beta drug and/or an anorectic agent.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770, 615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF), WO99/00353 (KaroBio) and GB98/284425 (KaroBio), with compounds of the KaroBio applications being preferred.

The anorectic agent which may be optionally employed in combination with compounds of the present invention include dexamphetamine, phentermine, phenylpropanolamine or mazindol, with dexamphetamine being preferred.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

Where the compounds of the invention are utilized in combination with one or more other therapeutic agent(s), either concurrently or sequentially, the following combination ratios and dosage ranges are preferred. Where the other antidiabetic agent is a biguanide, the compounds of formula I will be employed in a weight ratio to biguanide within the range from about 0.01:1 to about 100:1, preferably from about 0.1:1 to about 5:1.

The compounds of formula I will be employed in a weight ratio to the glucosidase inhibitor within the range from about 0.01:1 to about 100:1, preferably from about 0.5:1 to about 50:1.

The compounds of formula I will be employed in a weight ratio to the sulfonyl urea in the range from about 0.01:1 to about 100:1, preferably from about 0.2:1 to about 10:1.

The compounds of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compounds of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The DPP-IV inhibitor of formula I will be employed in a weight ratio to the meglitinide, PPAR-gamma agonist, PPAR-alpha/gamma dual agonist, aP2 inhibitor or SGLT2 inhibitor within the range from about 0.01:1 to about 100:1, preferably from about 0.2:1 to about 10:1.

The compounds of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from 1–4 times per day.

A typical injectable preparation may be produced by aseptically placing 250 mg of compounds of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitor activity of the compounds of the invention may be determined by use of an in vitro assay system which measures the potentiation of inhibition of DPP-4. Inhibition constants (Ki values) for the DPP-4 inhibitors of the invention may be determined by the method described below.

Purification of Porcine Dipeptidyl Peptidase IV

Porcine enzyme was purified as previously described (1), with several modifications. Kidneys from 15–20 animals were obtained, and the cortex was dissected away and frozen at −80° C. Frozen tissue (2000–2500 g) was homogenized in 12 L of 0.25 M sucrose in a Waring blender. The homogenate then was left at 37° C. for 18 hours to facilitate cleavage of DPP-4 from cell membranes. After the cleavage step, the homogenate was clarified by centrifugation at 7000×g for 20 min at 4° C., and the supernatant was collected. Solid ammonium sulfate was added to 60% saturation, and the precipitate was collected by centrifugation at 10,000×g and was discarded. Additional ammonium sulfate was added to the supernatant to 80% saturation, and the 80% pellet was collected and dissolved in 20 mM $Na_2HPO_4$, pH 7.4.

After dialysis against 20 mM $Na_2HPO_4$, pH 7.4, the preparation was clarified by centrifugation at 10,000×g. The clarified preparation then was applied to 300 mL of ConA Sepharose that had been equilibrated in the same buffer. After washing with buffer to a constant $A_{280}$, the column was eluted with 5% (w/v) methyl α-D-mannopyranoside. Active fractions were pooled, concentrated, and dialyzed against 5 mM sodium acetate, pH 5.0. Dialyzed material then was flowed through a 100 mL Pharmacia Resource S column equilibrated in the same buffer. The flow through material was collected and contained most of the enzyme activity. Active material again was concentrated and dialyzed into 20 mM $Na_2HPO_4$, pH 7.4. Lastly, the concentrated enzyme was chromatographed on a Pharmacia S-200 gel filtration column to removed low molecular weight contaminants. Purity of column fractions was analyzed by reducing SDS-PAGE, and the purest fractions were pooled and concentrated. Purified enzyme was stored in 20% glycerol at −80° C.

Assay of Porcine Dipeptidyl Peptidase IV

Enzyme was assayed under steady-state conditions as previously described (2) with gly-pro-p-nitroanilide as substrate, with the following modifications. Reactions contained, in a final volume of 100 μl, 100 mM Aces, 52 mM TRIS, 52 mM ethanolamine, 500 μM gly-pro-p-nitroanilide, 0.2% DMSO, and 4.5 nM enzyme at 25° C., pH 7.4. For single assays at 10 μM test compound, buffer, compound, and enzyme were added to wells of a 96 well microtiter plate, and were incubated at room temperature for 5 min. Reactions were started by addition of substrate. The continuous production of p-nitroaniline was measured at 405 nM for 15 min using a Molecular Devices Tmax plate reader, with a read every 9 seconds. The linear rate of p-nitroaniline production was obtained over the linear portion of each progress curve. A standard curve for p-nitroaniline absorbance was obtained at the beginning of each experiment, and enzyme catalyzed p-nitroaniline production was quantitated from the standard curve. Compounds giving greater than 50% inhibition were selected for further analysis.

For analysis of positive compounds, steady-state kinetic inhibition constants were determined as a function of both substrate and inhibitor concentration. Substrate saturation curves were obtained at gly-pro-p-nitroanilide concentrations from 60 μM to 3600 μM. Additional saturation curves also were obtained in the presence of inhibitor. Complete inhibition experiments contained 11 substrate and 7 inhibitor concentrations, with triplicate determinations across plates. For tight binding inhibitors with $K_i$s less than 20 nM, the enzyme concentration was reduced to 0.5 nM and reaction times were increased to 120 min. Pooled datasets from the three plates were fitted to the appropriate equation for either competitive, noncompetitive or uncompetitive inhibition.

(1) Rahfeld, J. Schutkowski, M., Faust, J., Neubert., Barth, A., and Heins, J. (1991) Biol. Chem. Hoppe-Seyler, 372, 313–318.

(2) Nagatsu, T., Hino, M., Fuyamada, H., Hayakawa, T., Sakakibara, S., Nakagawa, Y., and Takemoto, T. (1976) Anal. Biochem., 74, 466–476.

The following examples serve to better illustrate, but not limit, some of the preferred embodiments of the invention.

EXAMPLE 1

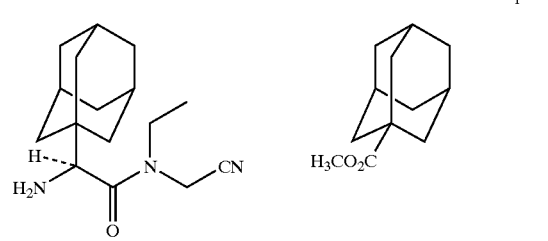

Step 1a

Adamantane-1-carboxylic acid (10.0 g, 55 mmol, 1 equiv) was dissolved in a mixture of $Et_2O$ (160 mL) and MeOH (40 mL), and was treated with trimethylsilyl diazomethane (2.0 M in hexane, 30 mL, 60 mmol, 1.1 equiv) and stirred at rt for 3 h. The volatiles were then removed by rotary evaporation and the product purified by flash column chromatography on silica gel (5×15 cm) with 40% CH₂Cl₂/hexanes to give the product as a white crystalline solid (10.7 g, 100%).

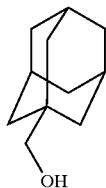

Step 1b

Compound 1b (10.7 g, 0.055 mmol, 1 equiv) was dissolved in anhydrous THF (150 mL) under argon and was treated with a solution of LiAlH₄ (1 M in THF, 69 mL, 69 mmol, 1.25 equiv). After stirring at rt for 1.5 h, the reaction was cooled to 0° C. and quenched sequentially with H₂O (5.1 mL), 15% aq NaOH (5.1 mL) and H₂O (10.2 mL). After stirring at rt for 15 min, the slurry was vacuum filtered and the solids washed with EtOAc (2×100 mL). The filtrate was concentrated by rotary evaporation on silica gel (5×15 cm) with 10% EtOAc/CH₂Cl₂ to provide compound 1b as a white solid (8.74 g, 96%).

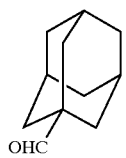

Step 1c

An oven-dried 3-neck flask equipped with 125-mL addition funnel was charged with anhydrous CH₂Cl₂ (150 mL) and anhydrous DMSO (10.3 mL, 0.145 mol, 2.5 equiv) under argon atmosphere and cooled to −78° C. Slow dropwise addition of oxalyl chloride (6.7 mL, 0.0768 mol, 1.32 equiv) followed by stirring for 15 min provided an activated DMSO adduct. This was treated with a solution of compound 1b (9.67 g, 58.2 mmol, 1 equiv) in dry CH₂Cl₂ (75 mL) and the reaction allowed to stir for 1 h. The resulting white mixture was then treated dropwise with triethylamine (40.5 mL, 0.291 mol, 5 equiv). After 30 min, the cooling bath was removed, and the reaction quenched sequentially with cold 20% aq KH₂PO₄ (25 mL) and cold H₂O (150 mL). After stirring at rt for 15 min the mixture was diluted with Et₂O (400 mL) and the layers were separated. The organics were washed with cold 10% aq KH₂PO₄ (3×150 mL) and satd aq NaCl (100 mL). Subsequently, the organics were dried (Na₂SO₄), filtered and concentrated. The residue was purified by flash column chromatography on silica gel (5×10 cm) with CH₂Cl₂ to give the Step 1c compound as a white solid (9.40 g, 98%).

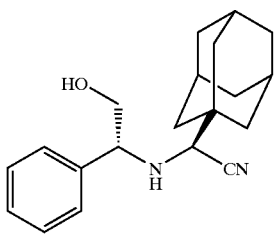

Step 1d

Compound 1c (9.40 g, 57 mmol, 1 equiv) was suspended in H₂O (145 mL) and cooled to 0° C. The mixture was treated with NaHSO₃ (5.95 g, 57 mmol, 1 equiv), KCN (4.0 g, 59 mmol, 1.04 equiv), and a solution of (R)-(−)-phenylglycinol (8.01 g, 57 mmol, 1 equiv) in MeOH (55 mL). The resulting mixture was stirred at rt for 2 h, then refluxed for 16 h. The mixture was cooled to rt, and 200 mL of EtOAc added. After mixing for 15 min the layers were separated. The aqueous fraction was extracted with EtOAc. The combined EtOAc extracts were washed with brine (50 mL), dried over anhydrous Na₂SO₄, filtered and the filtrate concentrated. The product was purified by flash column chromatography on silica gel (6.4×20 cm) with 20% EtOAc/hexanes to give the desired (R, S) product as a white solid (11.6 g, 37.4 mmol, 65%): MS m/e 311 (M+H)⁺.

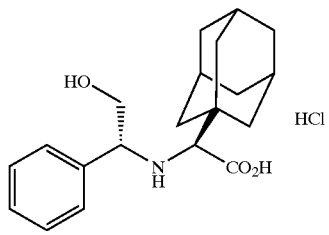

Step 1e

Compound 1d (5.65 g, 18 mmol) was heated in conc. HCl (120 mL) and HOAc (30 mL) at 80° C. for 18 h, at which time the reaction was cooled in an ice bath. Vacuum filtration of the resulting precipitate afforded the desired product as a white solid (5.21 g, 14 mmol, 78%). MS m/e 330 (m+H)⁺.

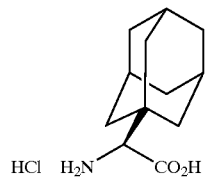

Step 1f

Compound 1e (5.21 g, 14 mmol) was dissolved in MeOH (50 mL) and HOAc (10 mL), and hydrogenated with H₂ (50 psi) and Pearlman's catalyst (20% Pd(OH)₂, 1.04 g, 20% w/w) for 18 h. The reaction was filtered through a PTFE membrane filter and the catalyst washed with MeOH (3×25 mL). The filtrate was concentrated by rotary evaporation to afford a white solid. The product was used in Step 7 without further purification.

Step 1g

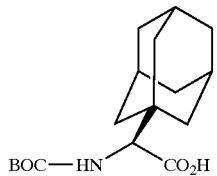

Compound 1f (≈14 mmol) was dissolved in anhydrous DMF (50 mL) under argon and treated with $K_2CO_3$ (5.90 g, 42 mmol, 3 equiv) and di-tert-butyldicarbonate (3.14 g, 14 mmol, 1 equiv) under argon at rt. After 19 h, the DMF was removed by rotary evaporation (0.2 mm Hg) and the residue dried further under reduced pressure. The residue was mixed with $H_2O$ (100 mL) and $Et_2O$ (100 mL), the layers separated, and the alkaline aqueous with $Et_2O$ (2×100 mL) to remove the by-product from the hydrogenolysis step. The aqueous was cooled to 0° C., diluted with EtOAc (200 mL), and stirred vigorously while carefully acidifying the aqueous to pH 3 with 1N aq HCl. The layers separated and the aqueous extracted with EtOAc (100 mL). The combined EtOAc extracts were washed with brine (50 mL), dried ($Na_2SO_4$), filtered and the filtrate concentrated by rotary evaporation. The residue was purified by $SiO_2$ flash column (5×12 cm) with 5% $MeOH/CH_2Cl_2$+0.5% HOAc. The product was chased with hexanes to afford the product as a white foam (4.07 g, 13 mmol, 92%): MS m/e 310 (m+H)$^+$.

Step 1h

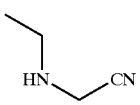

A 2 M solution of ethylamine in THF (4 mL, 8.0 mmol) was treated dropwise with bromoacetonitrile dropwise (0.48 g, 4.0 mmol) at rt. A slight exotherm in the reaction may be observed. The mixture was stirred overnight at rt and the mixture was stripped (15 mm Hg, 22° C.) to an oil. The remainder was diluted with ether and the organics washed with $NaHCO_3$ solution, dried ($Na_2SO_4$) and concentrated to an oil. The oil was purified by short path Kugelrohr distillation to prove compound In as a colorless oil: bp 40° C., 3 mm Hg. (0.13 g, 38%).

Step 1i

An oven-dried 15 mL test tube was charged with compound 1g (99 mg, 0.32 mmol), compound 1h (84 mg, 0.48 mmol), dimethylaminopyridine (37 mg, 0.32 mmol), 1-hydroxy-7-azabenzotriazole (65 mg, 0.48 mmol) and $CH_2Cl_2$ (2 mL). The tube was sealed under nitrogen atmosphere and treated with 1-[(3-(dimethyl)amino)propyl]-3-ethylcarbodiimide (92 mg, 0.48 mmol). The mixture was placed in a shaker and vortexed overnight. The mixture was diluted with 3 mL of $CH_2Cl_2$ and was washed with water, 5% citric acid solution, and half saturated $NaHCO_3$ soln. The organic fraction was dried ($Na_2SO_4$) and concentrated to an oil. The oil was purified by reverse phase preparative column chromatography on a YMC S5 ODS 20×250 mm column to provide compound 1i, 70 mg (58% yield). Purification conditions: Gradient elution from 10% acetonitrile/water/0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

Step 1j

An oven dried test tube was charged with compound 1i (45 mg, 0.12 mmol) and 0.4 mL of $CH_2Cl_2$ and 0.4 mL of triflouroacetic acid. The mixture was vortexed for 0.5 h and then concentrated to an oil. The oil was purified by reverse phase preparative column chromatography on a YMC S5 ODS 20×250 mm column to provide 13 mg (29% yield) of compound 1j. Purification conditions: Gradient elution from 10% acetonitrile/water/0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

Examples 2–8 were prepared using the methods described in Example 1

TABLE 2

| Example | Structure | [M + H] |
|---|---|---|
| 1 | 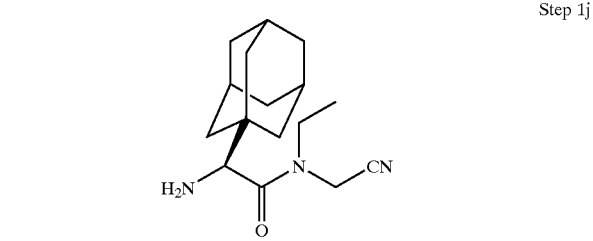 | 276$^+$ |

TABLE 2-continued

| Example | Structure | [M + H] |
|---|---|---|
| 2 | 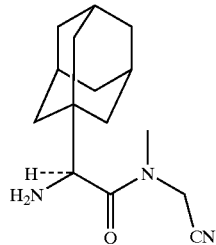 | 262+ |
| 3 | 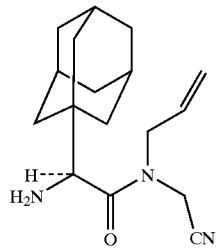 | 288+ |
| 4 | 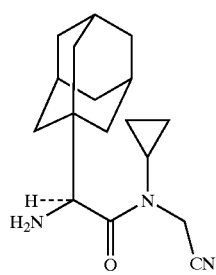 | 288+ |
| 5 | 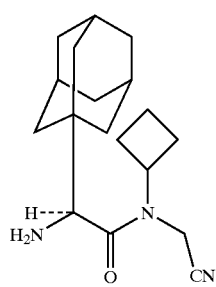 | 302+ |
| 6 | 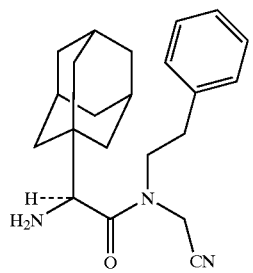 | 352+ |
| 7 | 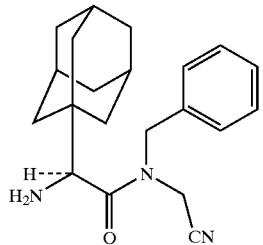 | 338+ |
| 8 | 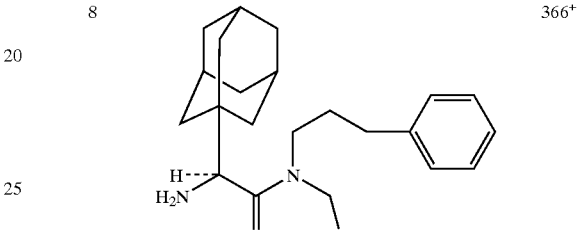 | 366+ |

EXAMPLE 9

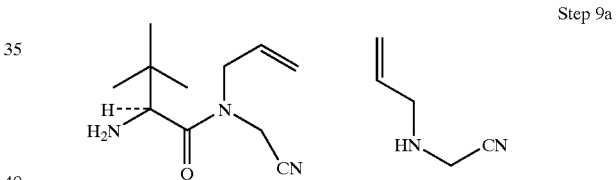

Step 9a

A solution of allylamine (1.83 g, 32.0 mmol) in THF (16 mL) was treated dropwise with bromoacetonitrile (1.92 g, 16.0 mmol) at rt. The mixture was stirred overnight at rt and the mixture was stripped (15 mm Hg, 22° C.) to an oil. The remainder was diluted with ether and the organics washed with NaHCO$_3$ solution, dried (Na$_2$SO$_4$) and concentrated to an oil. This afforded the compound 9a as a colorless oil. (1.0 g, 65%).

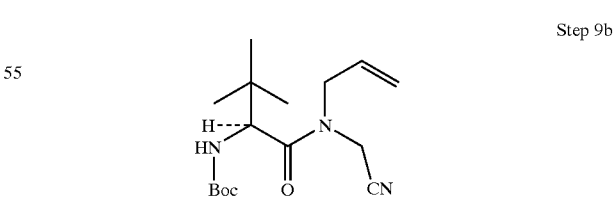

Step 9b

An oven-dried 15-mL test tube was charged with compound 9a (46 mg, 0.48 mmol), Boc-L-t-butyl-glycine (74 mg, 0.32 mmol), dimethylaminopyridine (37 mg, 0.32 mmol), 1-hydroxy-7-azabenzotriazole (65 mg, 0.48 mmol) and CH$_2$Cl$_2$ (2 mL). The tube was sealed under nitrogen atmosphere and treated with 1-[(3-(dimethyl)amino)propyl]-3-ethylcarbodiimide (92 mg, 0.48 mmol). The mixture was placed in a shaker and vortexed overnight. The mixture was diluted with 3 mL of $CH_2Cl_2$ and was washed with water, 5% citric acid solution, and half saturated $NaHCO_3$ soln. The organic fraction was dried ($Na_2SO_4$) and concentrated to an oil. The oil was purified by reverse phase preparative column chromatography on a YMC S5 ODS 20×250 mm column to provide compound 9b, 40 mg (40% yield). Purification conditions: Gradient elution from 10% acetonitrile/water/ 0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

Step 9c

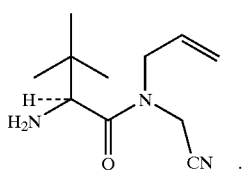

An oven dried test tube was charged with compound 9b (35 mg, 0.11 mmol) and 0.4 mL of $CH_2Cl_2$ and 0.4 mL of triflouroacetic acid. The mixture was vortexed for 0.5 h and then concentrated to an oil. The oil was purified by reverse phase preparative column chromatography on a YMC S5 ODS 20×250 mm column to provide compound 9c as the TFA salt, 20 mg (58% yield). Purification conditions: Gradient elution from 10% acetonitrile/water/0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

Examples 10–14 were prepared using the methods described in Example 9:

TABLE 3

| Example | Structure | [M + H] |
|---------|-----------|---------|
| 9 | 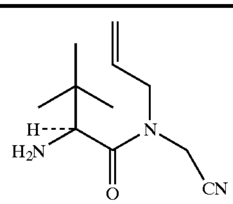 | 210+ |
| 10 | 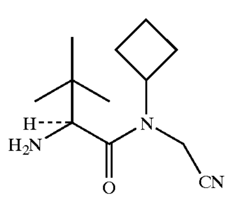 | 224+ |
| 11 | 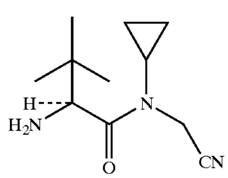 | 210+ |

TABLE 3-continued

| Example | Structure | [M + H] |
|---------|-----------|---------|
| 12 | 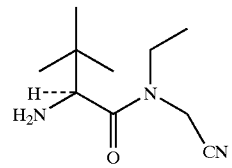 | 198+ |
| 13 | 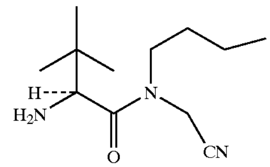 | 225+ |
| 14 | 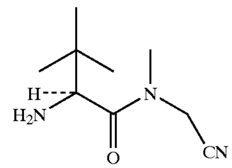 | 184+ |

EXAMPLE 15

Step 15a

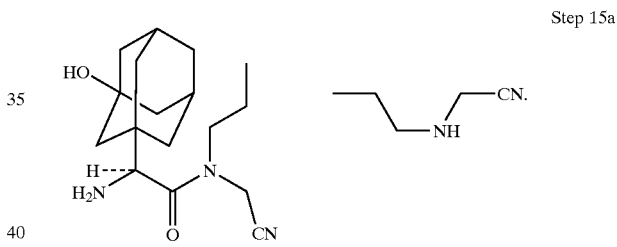

A solution of propylamine (1.89 g, 32.0 mmol) in THF (16 mL) was treated dropwise with bromoacetonitrile (1.92 g, 16.0 mmol) at rt. The mixture was stirred overnight at rt and the mixture was stripped (15 mm Hg, 22° C.) to an oil. The remainder was diluted with ether and the organics washed with $NaHCO_3$ solution, dried ($Na_2SO_4$) and concentrated to an oil to provide compound 15a as a colorless oil: (1.40 g, 89%).

Step 15b

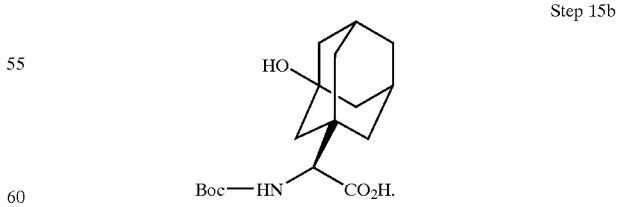

A solution of $KMnO_4$ (337 mg, 2.13 mmol, 1.1 equiv) in 2% aq KOH (6 mL) was heated to 60° C. and compound 1g (600 mg, 1.94 mmol, 1 equiv) was added in portions, and heating increased to 90° C. After 1.5 h, the reaction was cooled to 0° C., EtOAc (50 mL) was added, and the mixture was carefully acidified to pH 3 with 1N HCl. The layers were separated and the aqueous was extracted with EtOAc (50 mL). The combined organic extracts were washed with brine, dried over $Na_2SO_4$, filtered and concentrated. The residue was purified by flash column chromatography on silica gel (3.8×15 cm) with 2% (200 mL), 3% (200 mL), 4% (200 mL), and 5% (500 mL) $MeOH/CH_2Cl_2$+0.5% HOAc. After isolation of the product, the material was chased with hexanes to afford compound 15b as a white solid (324 mg, 51%): MS m/e 326 (m+H)$^+$.

Step 15c

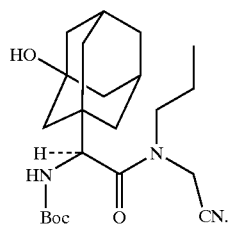

Compound 15a (94 mg, 0.95 mmol) was dissolved in anhydrous $CH_2Cl_2$ (4 mL) under nitrogen. The following were added in order: Compound 15b (208 mg, 0.64 mmol), HOAT (130 mg, 0.96 mmol), EDAC (184 mg, 0.96 mmol), and DMAP (74 mg, 0.64 mmol). The reaction mixture was vortexed overnight. The mixture was diluted with $CH_2Cl_2$ (5 mL), washed with citric acid solution, aq $NaHCO_3$ solution, dried over anhydrous $Na_2SO_4$, filtered and concentrated by rotary evaporation. The resulting oil was purified by reverse phase preparative column chromatography on a YMC S5 ODS 20×250 mm column to provide compound 15c 110 mg (42% yield). Purification conditions: Gradient elution from 10% acetonitrile/water/0.1 TFA to 90% acetonitrile/water/ 0.1 TFA over 15 min. 5 min. hold at 90% acetonitirle/water/ 0.1 TFA. Flow rate: 20 mL/min. Detection wavelength: 220 nm.

Step 15d

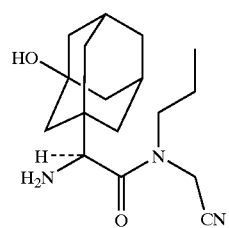

An oven dried test tube was charged with compound 15c (100 mg, 0.25 mmol) and 0.4 mL of $CH_2Cl_2$ and 0.4 mL of triflouroacetic acid. The mixture was vortexed for 0.5 h and then concentrated to an oil. The oil was triturated, and collected to give 26 mg (25%) of compound 15d as a white solid.

Examples 16–19 were prepared using the methods described in Example 15:

TABLE 4

| Example | Structure | [M + H] |
|---------|-----------|---------|
| 15 | 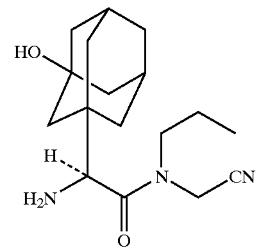 | 306$^+$ |
| 16 | 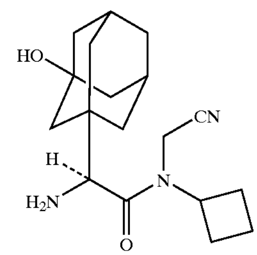 | 318$^+$ |
| 17 | 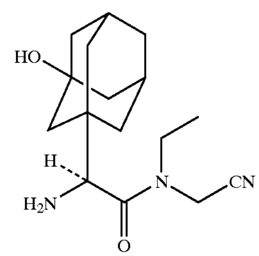 | 292$^+$ |
| 18 | 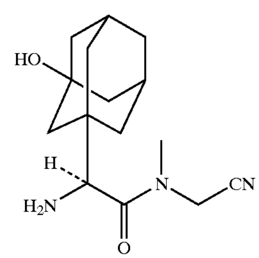 | 278$^+$ |
| 19 | 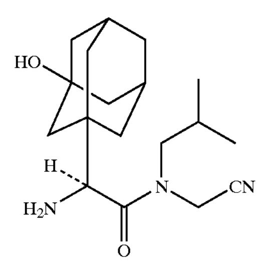 | 320$^+$ |

EXAMPLE 20

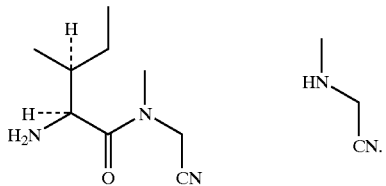

Step 20a

Starting compound 20a was commercially purchased from TCI America, Portland Oreg., USA.

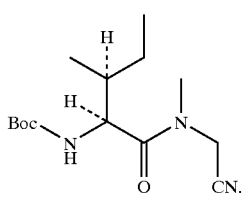

Step 20b

Compound 20a compound (34 mg, 0.48 mmol) was dissolved in anhydrous $CH_2Cl_2$ (4 mL) under nitrogen. The following were added in order: N-Boc-L-isoleucine (74 mg, 0.32 mmol), HOAT (65 mg, 0.48 mmol), EDAC (92 mg, 0.48 mmol), and DMAP (37 mg, 0.32 mmol). The reaction mixture was vortexed overnight. The mixture was diluted with $CH_2Cl_2$ (5 mL), washed with citric acid solution, aq $NaHCO_3$ solution, dried over anhydrous $Na_2SO_4$, filtered and concentrated by rotary evaporation to provide compound 20b as a crude oil. (50 mg). Compound 20b was used in step 3 without further purification.

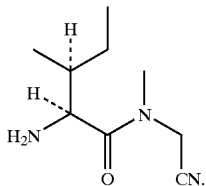

Step 20c

An oven dried test tube was charged with Compound 20c (50 mg, 0.17 mmol) and 0.4 mL of $CH_2Cl_2$ and 0.4 mL of triflouroacetic acid. The mixture was vortexed for 0.5 h and then concentrated to an oil. The oil was purified by reverse phase preparative column chromatography on a YMC S5 ODS 20×250 mm column to provide compound 20c as the TFA salt, 24 mg (48% yield). Purification conditions: Gradient elution from 10% acetonitrile/water/0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

Examples 21 & 22 were prepared by the method outlined in Example 20 using commercially available Boc-amino acids.

TABLE 5

| Example | Structure | [M + H] |
|---|---|---|
| 20 | 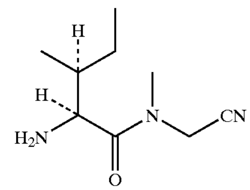 | 184+ |
| 21 | 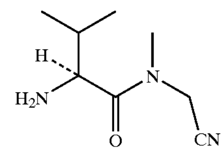 | 170+ |
| 22 | 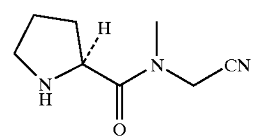 | 168+ |

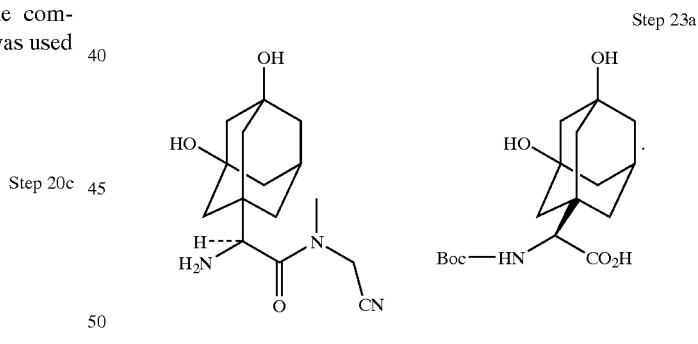

EXAMPLE 23

Step 23a

A solution of $KMnO_4$ (337 mg, 2.13 mmol, 1.1 equiv) in 2% aq KOH (6 mL) was heated to 60° C. and compound 1 g (600 mg, 1.94 mmol, 1 g equiv) was added in portions, while increasing the temperature to 90° C. After 1.5 h, the reaction was cooled to 0° C., EtOAc (50 mL) was added, and the mixture was carefully acidified to pH 3 with 1N HCl. The layers were separated and the aqueous was extracted with EtOAc (50 mL). The combined organic extracts were washed with brine, dried over $Na_2SO_4$, filtered and concentrated. The residue was purified by flash column chromatography on silica gel (3.8×15 cm) with 2% (200 mL), 3% (200 mL), 4% (200 mL), and 5% (500 mL) MeOH/ $CH_2Cl_2$+0.5% HOAc. After isolation of the product, the material was chased with hexanes to afford compound 23a as a white solid (120 mg, 15%): MS m/e 326 (m+H)+.

EXAMPLE 24

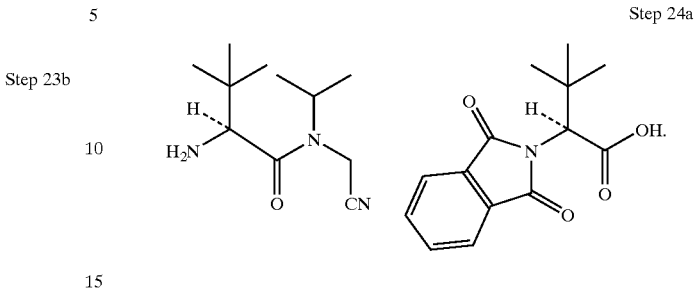

Step 24a

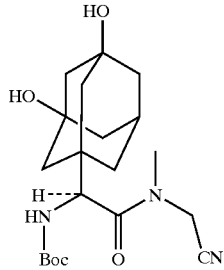

Step 23b

Phthalic anhydride (1.0 g, 7.63 mmol) was diluted with toluene (2 mL) and treated with L-tert-butylglycine (1.13 g, 7.63 mmol). The mixture was heated to 120° C. for 4 h and cooled to rt where a white solid formed. The solid was collected and purified by flash column chromatography (1:9 methanol:CH$_2$Cl$_2$) on silica gel to provide compound 24a as a white solid, 1.55 g, 78% yield.

Compound 20a (21 mg, 0.30 mmol) was dissolved in anhydrous CH$_2$Cl$_2$ (4 mL) under nitrogen. The following were added in order: compound 23a (68 mg, 0.20 mmol), HOAT (41 mg, 0.30 mmol), EDAC (58 mg, 0.30 mmol), and DMAP (24 mg, 0.20 mmol). The reaction mixture was vortexed overnight filtered and concentrated by rotary evaporation. The oil was purified by reverse phase preparative column chromatography on a YMC S5 ODS 20×250 mm column to provide compound 23b: 17 mg (21% yield). Purification conditions: Gradient elution from 1% acetonitrile/water/0.1 TFA to 90% acetonitrile/water/0.1 TFA over 15 min. 5 min. Hold at 90% acetonitirle/water/0.1 TFA. Flow rate: 20 mL/min. Detection wavelength: 220 nm.

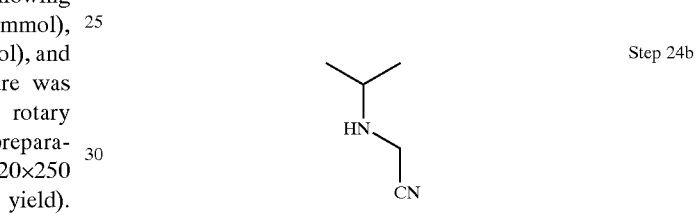

Step 24b

A solution of iso-propylamine (1.89 g, 32.0 mmol) in THF (16 mL) was treated dropwise with bromoacetonitrile (1.92 g, 16.0 mmol) at rt. The mixture was stirred overnight at rt and the mixture was stripped (15 mm Hg, 22° C.) to an oil. The remainder was diluted with ether and the organics washed with NaHCO$_3$ solution, dried (Na$_2$SO$_4$) and concentrated to provide compound 24b as a colorless oil (1.50 g, 95%).

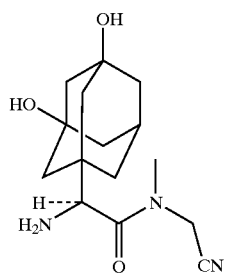

Step 23c

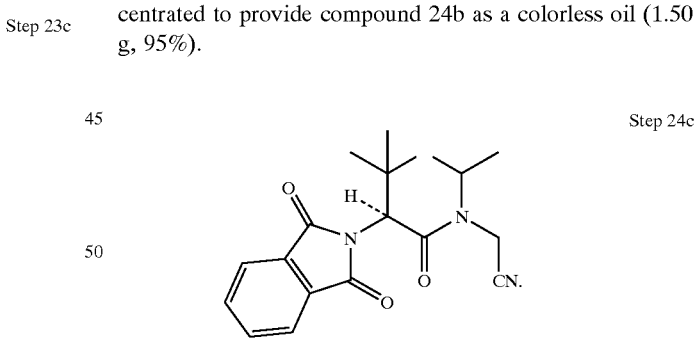

Step 24c

An oven dried test tube was charged with compound 23b (15 mg, 0.04 mmol) and 0.4 mL of CH$_2$Cl$_2$ and 0.4 mL of triflouroacetic acid. The mixture was vortexed for 0.5 h and then concentrated. The remainder was purified by reverse phase preparative column chromatography on a YMC S5 ODS 20×250 mm column to provide compound 23c: 6 mg (40% yield). Purification conditions: Gradient elution from 1% acetonitrile/water/0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

An oven-dried 10-mL round-bottomed flask was charged CH$_2$Cl$_2$ (2 mL), Compound 24a (141 mg, 0.54 mmol), and then oxalyl chloride in CH$_2$Cl$_2$ (540 µL, 1.08 mmol). The mixture was stirred for 0.5 h at rt and treated with DMF (10 µL, catalyst) after which time, the mixture was concentrated under reduced pressure. The remainder was diluted with CH$_2$Cl$_2$ (2 mL) and then reacted with Hunigs base (280 mg, 2.16 mmol), DMAP (66 mg, 0.54 mmol) and compound 24b (159 mg, 1.62 mmol). The reaction mixture was stirred overnight at rt and quenched with water. The organic layer was diluted with CH$_2$Cl$_2$ and washed with H$_2$O, 10% citric acid, NaHCO₃ solution, and dried over Na₂SO₄. Purification by flash column chromatography on silica gel (gradient from hexane to EtOAc) provided compound 24c (20 mg).

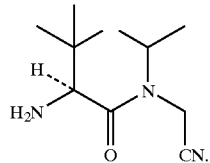

24d

The reaction of compound 24c with H₂N—NH₂ (5 equivalents) in methanol for 5 days yields the compound 24d.

EXAMPLE 25

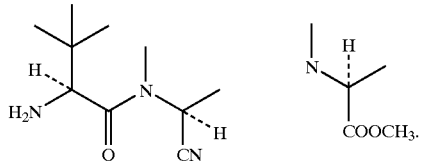

Step 25a

A mixture of methanol (20 mL) and N-methyl-L-alanine (2.0 g, 20 mmol) was treated with HCl gas until saturated. The mixture was allowed to stand overnight at rt. The methanol was removed under reduced pressure to give compound 25a as a thick oil (3.00 g) (95% conc. as evaluated by NMR).

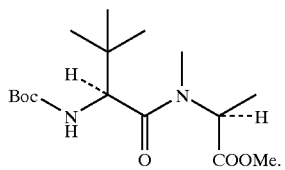

Step 25b

An oven-dried 15-mL round-bottom flask was charged with compound 25a (0.66 g, 4.30 mmol), and N-Boc-L-tert-butylglycine (1.00 g, 4.30 mmol), dimethylaminopyridine (0.30 g, 2.5 mmol), 1-hydroxy-7-azabenzotriazole (0.58 g, 4.30 mmol), triethylamine (1.75 mL, 12.00 mmol) and DMF (5 mL). The round-bottomed flask was sealed under nitrogen atmosphere and treated with 1-[(3-(dimethyl)amino)propyl]-3-ethylcarbodiimide (1.14 g, 6.00 mmol). The mixture was stirred overnight and diluted with equal portions of EtOAc and water (30 mL). The organic fraction was washed with water, 5% citric acid solution, and half saturated NaHCO₃ soln, dried (Na₂SO₄) and concentrated to an oil. The oil was purified by silica gel colunm chromatography with a gradient from 1:9 EtOAc:hexane to 3.5:6.5 EtOAc:hexane to provide 0.50 g (35% yield) of compound 25b.

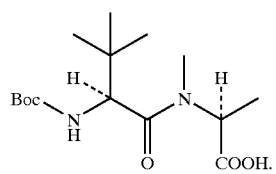

Step 25c

A solution of compound 25b (0.50 g, 1.50 mmol) in methanol (5 mL) and water (2 mL) was treated with NaOH (0.5 g, 12.5 mmol) and heated to 50° C. After 0.5 hours the mixture was cooled to rt and acidified to pH=3 with KHSO₄ solution. The organics were extracted with EtOAc, dried over MgSO₄, and concentrated to give 0.48 g (100%) of the title compound.

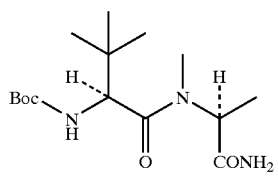

Step 25d

To a stirred solution of compound 25c (0.48 g, 1.52 mmol) in THF (6 mL) at −15° C. under nitrogen, was added 4-methylmorpholine (0.22 mL, 2.00 mmol) and then isobutyl chloroformate (0.25 mL, 0.1.90 mmol) over 2 min to form a white precipitate. The reaction mixture was stirred at −15° C. under nitrogen for 25 min and a solution of NH₃ in dioxane (8.0 mL, 4.0 mmol) was added. Following, the reaction mixture was stirred at −15° C. for 30 min, warmed to rt and stirred at rt overnight. The reaction mixture was quenched by 4% KHSO₄ to ~pH 4 and extracted with EtOAc (20 mL×3). The extracts were combined, washed with brine (10 mL), dried (Na₂SO₄) and evaporated to provide an oil. The oil was purified by reverse phase preparative column chromatography on a YMC S5 ODS 20×250 mm column to provide compound 25d: 400 mg (83% yield). Purification conditions: Gradient elution from 20% acetonitrile/water/ 0.1 TFA to 90% acetonitrile/water/0.1 TFA over 15 min. 5 min. hold at 90% acetonitirle/water/0.1 TFA. Flow rate: 20 mL/min. Detection wavelength: 220 nm.

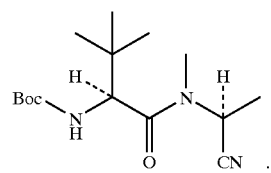

Step 25e

To a stirred solution of compound 25d (0.40 g, 1.20 mmol) and imidazole (0.16 g, 1.38 mmol) in dry pyridine (4 mL) at −35° C. under nitrogen was added POCl₃ (0.46 mL, 4.8 mmol) to provide a thick slurry. The slurry mixture was stirred between −35° C. to −20° C. for 1 h and evaporated. The remainder was diluted with EtOAc and washed with water, citric acid and NaHCO₃ solutiuon. The organic fraction was dried (Na$_2$SO$_4$), concentrated and purified by flash chromatography on silica gel (1:9 to 3:7 EtOAc/hexane) to provide compound 25e as a colorless oil, 0.19 g, 48% yield.

Step 25f

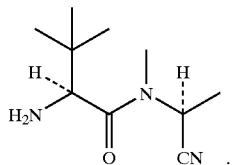

An 10 mL round-bottom flask was charged with compound 25e (150 mg, 0.45 mmol) and 2 mL of CH$_2$Cl$_2$ and 2 mL of triflouroacetic acid. The mixture was stirred for 0.5 h and then concentrated. The remainder was purified by reverse phase preparative column chromatography on a YMC S5 ODS 20×250 mm column to provide compound 27f 15 mg (10% yield). Purification conditions: Gradient elution from 10% methanol/water/0.1 TFA to 90% methanol/water/0.1 TFA over 10 min. 5 min. Hold at 90% methanol/water/0.1 TFA. Flow rate: 20 mL/min. Detection wavelength: 220 nm.

What is claimed is:

1. A compound of the formula I:

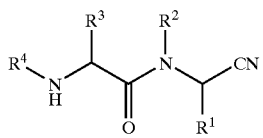

wherein:
  R$^1$ is selected from the group consisting of hydrogen (H), C$_1$–C$_6$ alkyl, C$_1$–C$_6$ alkenyl, C$_1$–C$_6$ alkynyl, C$_3$–C$_8$ cycloalkyl and C$_3$–C$_8$ cycloalkenyl;
  R$^2$ is a substituted or unsubstituted functional group selected from the group consisting of C$_1$–C$_6$ alkyl, C$_3$–C$_8$ cycloalkyl, C$_3$–C$_8$ cycloalkenyl, alkenyl, alkynyl, aryl, arylalkyl, arylalkenyl and arylalkynyl;
  R$^3$ is selected from the group consisting of alkyl, alkenyl, alkynyl, cycloalkyl, cycloalkylalkyl, alkylthioalkyl, arylalkylthioalkyl, cycloalkenyl, aryl, arylalkyl, arylalkenyl, arylalkynyl, heteroaryl, heteroarylalkyl, cycloheteroalkyl and cycloheteroalkylalkyl, wherein any R$^3$ group may optionally be substituted through any available carbon atom with 1 to 5 substituents selected from the group consisting of hydrogen, halo, alkyl, polyhaloalkyl, alkoxy, haloalkoxy, alkoxycarbonyl, alkenyl, alkynyl, cycloalkyl, cycloalkylalkyl, heteroarylamino, —N(R$^5$)Ar, cycloheteroalkyl, cycloheteroalkylalkyl, OR$^5$, hydroxyalkyl, nitro, cyano, NR$^5$R$^{5'}$, alkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;
  R$^4$ is hydrogen (H), or R$^4$ can be taken together with R$^3$ to form a substituted or unsubstituted 4 to 5 membered heterocyclic ring, preferably substituted by NR$^5$R$^{5'}$ or C$_1$–C$_6$ alkyl; and R$^5$ and R$^{5'}$ for each occurrence are each independently selected from the group consisting of hydrogen, alkyl, alkenyl, alkynyl, cycloalkyl, aryl, arylalkyl, arylalkenyl, arylalkynyl, heterocycle and heteroaryl.
including all prodrug esters, pharmaceutically acceptable salts and stereoisomers thereof.

2. The compound as defined in claim 1 wherein
  R$^1$ is H or C$_1$–C$_6$ alkyl;
  R$^2$ is C$_1$–C$_6$ alkyl;
  R$^3$ is alkyl or cycloalkyl; and
  R$^4$ is H.

3. The compound as defined in claim 1 wherein
  R$^1$ is H;
  R$^2$ is C$_1$–C$_6$ alkyl;
  R$^3$ is a cycloalkyl containing 6 to 15 carbons; and
  R$^4$ is H.

4. The compound as defined in claim 1 having the structure:

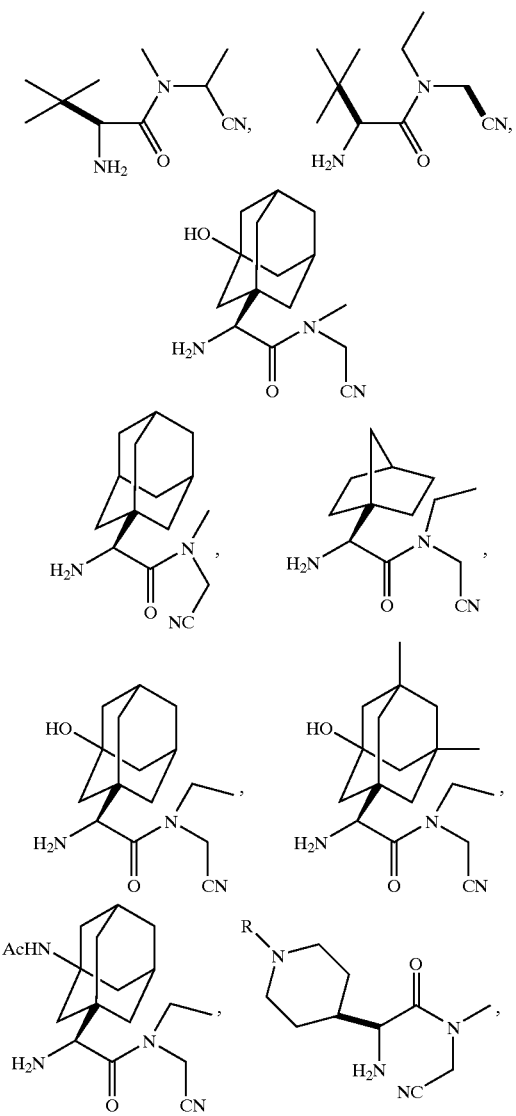

-continued

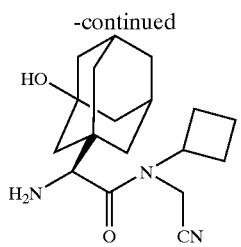

including all pharmaceutically acceptable salts and stereoisomers thereof.

5. The compounds as defined in claim 3 wherein the pharmaceutically acceptable salt is the hydrochloride salt or the trifluoroacetic acid salt.

6. A pharmaceutical composition comprising a compound as defined in claim 1 and a pharmaceutically acceptable carrier therefor.

7. A pharmaceutical combination comprising a compound as defined in claim 1 and at least one therapeutic agent selected from the group consisting of an antidiabetic agent, an anti-obesity agent, a anti-hypertensive agent, an anti-atherosclerotic agent and a lipid-lowering agent.

8. The pharmaceutical combination as defined in claim 7 comprising the compound as defined in claim 1 and an antidiabetic agent.

9. The combination as defined in claim 8 wherein the antidiabetic agent is at least one agent selected from the group consisting of a biguanide, a sulfonyl urea, a glucosidase inhibitor, a PPAR γ agonist, a PPAR α/γ dual agonist, an aP2 inhibitor, a SGLT2 inhibitor, an insulin sensitizer, a glucagon-like peptide-1 (GLP-1), insulin and a meglitinide.

10. The combination as defined in claim 9 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinide, nateglinide, KAD 1129, AR-HO39242, GW-409544, KRP297, AC2993, LY315902, and NVP-DPP-728A.

11. The combination as defined in claim 8 wherein the compound is present in a weight ratio to the antidiabetic agent in the range of about 0.01 to about 300:1.

12. The combination as defined in claim 7 wherein the anti-obesity agent is at least one agent selected from the group consisting of a beta 3 adrenergic agonist, a lipase inhibitor, a serotonin (and dopamine) reuptake inhibitor, a thyroid receptor beta compound, and an anorectic agent.

13. The combination as defined in claim 12 wherein the anti-obesity agent is at least one agent selected from the group consisting of orlistat, ATL-962, AJ9677, L750355, CP331648, sibutramine, topiramate, axokine, dexamphetamine, phentermine, phenylpropanolamine and mazindol.

14. The combination as defined in claim 7 wherein the lipid lowering agent is at least one agent selected from the group consisting of an MTP inhibitor, cholesterol ester transfer protein, an HMG CoA reductase inhibitor, a squalene synthetase inhibitor, a fibric acid derivative, an upregulator of LDL receptor activity, a lipoxygenase inhibitor, or an ACAT inhibitor.

15. The combination as defined in claim 14 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, TS-962, MD-700, CP-529414, and/or LY295427.

16. The combination as defined in claim 14 wherein the compound as defined in claim 1 is present in a weight ratio to the lipid-lowering agent in the range of about 0.01 to about 100:1.

17. A method for treating or delaying the progression or onset of diabetes, diabetic retinopathy, diabetic neuropathy, diabetic nephropathy, wound healing, insulin resistance, hyperglycemia, hyperinsulinemia, Syndrome X, diabetic complications, elevated blood levels of free fatty acids or glycerol, hyperlipidemia, obesity, hypertriglyceridemia, atherosclerosis or hypertension, which comprises administering to a mammalian species in need of treatment a therapeutically effective amount of a compound as defined in claim 1.

18. A method according to claim 17 further comprising administering, concurrently or sequentially, a therapeutically effective amount of at least one additional therapeutic agent selected from the group consisting of an antidiabetic agent, an anti-obesity agent, a anti-hypertensive agent, an anti-atherosclerotic agent and a lipid-lowering agent.

* * * * *